United States Patent
Asai et al.

(10) Patent No.: US 11,214,559 B2
(45) Date of Patent: Jan. 4, 2022

(54) METHOD FOR PRODUCING 2,5-BIS(AMINOMETHYL)FURAN

(71) Applicant: Mitsubishi Gas Chemical Company, Inc., Tokyo (JP)

(72) Inventors: Ryo Asai, Tokyo (JP); Tomoaki Kirino, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 67 days.

(21) Appl. No.: 16/631,763

(22) PCT Filed: Jul. 20, 2018

(86) PCT No.: PCT/JP2018/027251
§ 371 (c)(1),
(2) Date: Jan. 16, 2020

(87) PCT Pub. No.: WO2019/017468
PCT Pub. Date: Jan. 24, 2019

(65) Prior Publication Data
US 2020/0181105 A1    Jun. 11, 2020

(30) Foreign Application Priority Data

Jul. 21, 2017    (JP) .............. JP2017-141976

(51) Int. Cl.
C07D 307/52    (2006.01)
B01J 25/02    (2006.01)

(52) U.S. Cl.
CPC ............. *C07D 307/52* (2013.01); *B01J 25/02* (2013.01)

(58) Field of Classification Search
CPC ................. C07D 307/52; B01J 25/02
See application file for complete search history.

(56) References Cited

U.S. PATENT DOCUMENTS

| | | | |
|---|---|---|---|
| 9,988,491 B2* | 6/2018 | Klein | C08G 69/48 |
| 10,407,547 B2* | 9/2019 | Masuno | C07C 209/68 |
| 10,662,142 B2* | 5/2020 | Li | B01J 37/0236 |

FOREIGN PATENT DOCUMENTS

| | | |
|---|---|---|
| CN | 104277018 A | 1/2015 |
| KR | 20160034084 A | 3/2016 |
| WO | 03/024947 A1 | 3/2003 |
| WO | 2012/004069 A1 | 1/2012 |
| WO | 2016/068712 A1 | 5/2016 |

OTHER PUBLICATIONS

International Preliminary Report on Patentability and Written Opinion for PCT/JP2018/027251, dated Oct. 9, 2018, and English Translation submitted herewith (9 pages).
International Search Report for PCT/JP2018/027251, dated Oct. 9, 2018, and English Translation submitted herewith (4 pages).
Brasholz, Malte et al., "Highly efficient dehydration of carbohydrates to 5-(chloromethyl)furfural (CMF), 5-(hydroxymethyl)furfural (HMF) and levulinic acid by biphasic continuous flow processing," Green Chemistry, 2011, vol. 13, No. 5, pp. 1114-1117.
El Hajj, Toni et al., "Synthèse de l'hydroxyméthyl-5 furanne carboxaldéhyde-2 et de ses dérivés par traitement acide de sucres sur résines échangeuses d'ions," Bulletin de la Société Chimique de France, 1987, No. 5, pp. 855-860.
Le, Ngoc-Thuc et al., "Preparation of 2,5-Bis(Aminomethyl)Furan by Direct Reductive Amination of 2,5-Diformylfuran over Nickel-Raney Catalysts," Green and Sustainable Chemistry, 2015, vol. 5, pp. 115-127.
Extended European Search Report issued in corresponding European Application No. 18835526.7 dated May 4, 2020 (7 pages).

* cited by examiner

*Primary Examiner* — D Margaret M Seaman
(74) *Attorney, Agent, or Firm* — Fitch, Even, Tabin & Flannery LLP

(57) ABSTRACT

The present invention is to provide a production method that can produce 2,5-bis(aminomethyl)furan efficiently. The production method for 2,5-bis(aminomethyl)furan includes reacting 5-(halogenated methyl)furfural with hydrogen and an amine compound using a hydrogenation catalyst to obtain 2,5-bis(aminomethyl)furan.

22 Claims, No Drawings

METHOD FOR PRODUCING 2,5-BIS(AMINOMETHYL)FURAN

CROSS-REFERENCE TO RELATED APPLICATIONS

This application is a U.S. national phase application filed under 35 U.S.C. § 371 of International Application Number PCT/JP2018/027251, filed Jul. 20, 2018, designating the United States, which claims priority from Japanese Application Number 2017-141976, filed Jul. 21, 2017.

FIELD OF THE INVENTION

The present invention relates to a method for producing 2,5-bis(aminomethyl)furan.

BACKGROUND OF THE INVENTION

Furan derivatives, which are compounds having a furan ring, are useful as raw materials and intermediate products of resins, pharmaceuticals, perfumes, and the like. For example, 2,5-(hydroxymethyl)furfural (hereinafter, also referred to as "HMF"), a furan derivative, can be obtained from fructose, which is a saccharide, as described in Patent Document 1, and is a versatile intermediate product that can be prepared from biomass feedstocks such as naturally occurring carbohydrates.

Since such biomass feedstocks are available at low cost and better than fossil fuels from the perspective of environmental protection, the biomass feedstocks attract attention as raw materials for resins and the like.

It has been studied to obtain a versatile furan derivative by further performing a functional group transformation reaction of HMF, and methods for producing 2,5-bis(aminomethyl)furan (hereinafter, also referred to as "BAF") are described in, for example, Patent Document 2 and Non-Patent Document 1.

Non-Patent Document 1 specifically describes that BAF can be synthesized by oxidization of HMF to obtain 2,5-diformylfuran before reductive amination by using a hydrogen peroxide-treated Raney nickel as a catalyst.

Patent Document 2 also describes that BAF can be synthesized by using a catalyst, such as Raney nickel, Mo-Raney nickel, Raney cobalt, copper, copper-nickel, or ruthenium, for 2,5-diformylfuran.

CITATION LIST

Patent Literature

Patent Document 1: WO 2003-024947
Patent Document 2: KR 2016-0034084 A

Non-Patent Literature

Non-Patent Document 1: Green and Sustainable Chemistry, 2015, 5, 115-127.

SUMMARY OF INVENTION

The production methods which Non-Patent Document 1 and Patent Document 2 disclose, in case where using HMF as a starting material, require a two-step reaction from HMF to obtain BAF, which includes oxidization of a hydroxy group and reductive amination of an aldehyde. Therefore, there is a need for an efficient production method of BAF.

The present invention was completed in view of the circumstances described above, and an object of the present invention is to provide a production method that can efficiently produce BAF.

As a result of diligent research on the method for producing BAF, the present inventors found that the BAF could be obtained in one-pot by subjecting 5-(halogenated methyl)furfural to a reductive amination reaction, and thus BAF could be efficiently produced. Therefore, the present invention was completed.

That is, the present invention is as follows.

[1] A production method for 2,5-bis(aminomethyl)furan, including reacting 5-(halogenated methyl)furfural with hydrogen and an amine compound using a hydrogenation catalyst to obtain 2,5-bis(aminomethyl)furan.

[2] The production method according to [1], wherein the 5-(halogenated methyl) furfural is 5-(chloromethyl)furfural.

[3] The production method according to [1] or [2], wherein the 5-(halogenated methyl)furfural is derived from at least one type selected from the group consisting of woody biomass, cellulose, and C6 saccharides that are saccharides having 6 carbon atoms.

[4] The production method according to any one of [1] to [3], wherein the amine compound is ammonia or an amide represented by $RCONH_2$, where R represents a hydrogen atom or $-C_nH_{2n+1}$ (n is an integer of 1 or more).

[5] The production method according to any one of [1] to [4], wherein the hydrogenation catalyst is a catalyst containing at least one type selected from the group consisting of Fe, Co, Ni, Cu, Ru, Rh, Pd, Ir, Pt, Re, and Os.

[6] The production method according to any one of [1] to [5], wherein the reaction is performed at a hydrogen pressure of more than 0 MPaG and 25 MPaG or less.

[7] The production method according to any one of [1] to [5], wherein the reaction is performed at a hydrogen pressure of more than 0 MPaG and less than 9 MPaG.

[8] The production method according to any one of [1] to [7], further including separating 2,5-bis(aminomethyl)furan from the catalyst.

The production method of the present invention is possible to provide BAF efficiently and is an industrially advantageous production method. Furthermore, since the 5-(halogenated methyl)furfural may be formed by using a natural product derived from biomass feedstocks, as its raw material, the production method of the present invention has little environmental load. Furthermore, BAF obtained by the production method of the present invention is useful as a raw material and an intermediate product of resins, pharmaceuticals, perfumes, and the like.

DESCRIPTION OF EMBODIMENTS

Embodiments of the present invention (hereinafter, referred to as "present embodiment") are described in detail below; however, the present invention is not limited to the embodiments, and various modifications may be made without departing from the scope and spirit of the invention.

The production method of the present embodiment is a production method for 2,5-bis(aminomethyl)furan, the method including reacting 5-(halogenated methyl)furfural with hydrogen and an amine compound using a hydrogenation catalyst to obtain 2,5-bis(aminomethyl)furan.

According to the production method of the present embodiment, 2,5-bis(aminomethyl)furan can be produced in one reaction system from 5-(halogenated methyl) furfural.

(2,5-Bis(aminomethyl)furan)

2,5-bis(aminomethyl)furan in the present embodiment can be represented by Formula (1).

[Chemical Formula 1]

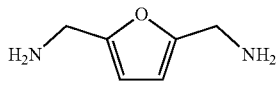

(1)

(5-(Halogenated methyl)furfural)

The 5-(halogenated methyl)furfural in the present embodiment can be represented by Formula (2).

[Chemical Formula 2]

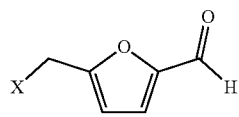

(2)

In Formula (2), X is a halogen atom selected from the group consisting of chlorine, bromine, and iodine.

In the 5-(halogenated methyl)furfural in the present embodiment, X in Formula (2) is preferably chlorine. That is, the 5-(halogenated methyl)furfural is preferably 5-(chloromethyl)furfural.

The 5-(halogenated methyl)furfural is derived from at least one type selected from the group consisting of woody biomass, cellulose, and C6 saccharides that are saccharides having 6 carbon atoms. The 5-(halogenated methyl)furfural can be obtained by derivatization of these.

Specifically, the 5-(halogenated methyl)furfural can be obtained from a C6 saccharide that is a saccharide having 6 carbon atoms, and the C6 saccharide that is a saccharide having 6 carbon atoms can be easily obtained from cellulose which is a main constituent of woody biomass.

Woody biomass means "biomass feedstock formed from wood" and is a widely existing resource in the world.

The 5-(halogenated methyl)furfural can be obtained in a one-step reaction by hydrolysis of cellulose, for example. When the 5-(halogenated methyl)furfural is obtained by hydrolysis of cellulose, specifically, the 5-(halogenated methyl)furfural can be obtained by reacting cellulose with hydrogen halide, such as hydrogen chloride, hydrogen bromide, and hydrogen iodide in a water solvent. Commercially available products may be used as the 5-(halogenated methyl)furfural.

The 5-(halogenated methyl)furfural can be obtained in a one-step reaction by reacting woody biomass with a hydrogen halide, such as hydrogen chloride, hydrogen bromide, or hydrogen iodide, to perform hydrolysis.

Furthermore, the 5-(halogenated methyl)furfural can be obtained by reacting a C6 saccharide, which is a saccharide including 6 carbons atoms, with a hydrogen halide. Examples of the C6 saccharide include glucose and fructose. The 5-(halogenated methyl)furfural can be obtained by, for example, performing a two-step reaction, in which a C6 saccharide is used to form an HMF as described in WO 2003-024947 and then a hydroxy group in the HMF is subjected to a halogenation reaction such as the Appel reaction. Furthermore, similar to the method for obtaining the 5-(halogenated methyl)furfural from cellulose, the 5-(halogenated methyl)furfural can be obtained in a one-step reaction by reacting a C6 saccharide with a hydrogen halide, such as hydrogen chloride, hydrogen bromide, or hydrogen iodide in a water solvent.

(Amine Compound)

The amine compound in the present embodiment is preferably ammonia ($NH_3$) and/or amide represented by $RCONH_2$, where R represents a hydrogen atom or $-C_nH_{2n+1}$ (n is an integer of 1 or more), and is more preferably ammonia.

In $-C_nH_{2n+1}$, is preferably from 1 to 20, and more preferably from 1 to 10.

(Hydrogenation Catalyst)

The hydrogenation catalyst in the present embodiment is not particularly limited as long as the hydrogenation catalyst is the one typically used as a catalyst in a catalytic hydrogenation reaction. The hydrogenation catalyst preferably contains a metal, such as Fe, Co, Ni, Cu, Ru, Rh, Pd, Ir, Pt, Re, or Os. One type of these metals may be used alone, or a combination of two or more types of these metals may be used.

The metal described above may be supported by a carrier. The carrier is not particularly limited as long as the carrier is one typically used as a catalyst carrier, and examples thereof include inorganic oxides, activated carbon, and ion exchange resins. Specific examples of the inorganic oxide include silica ($SiO_2$), titania ($TiO_2$), zirconia ($ZrO_2$), alumina ($Al_2O_3$), magnesium oxide (MgO), and complexes of two or more types of these inorganic oxides (e.g., zeolite).

Specific examples of the hydrogenation catalyst include iron (Fe) catalysts, such as reduced iron; cobalt (Co) catalysts, such as reduced cobalt and Raney cobalt; nickel (Ni) catalysts, such as reduced nickel, nickel oxide, and Raney nickel (hereinafter, also referred to as "Raney-Ni"); copper (Cu) catalysts, such as copper(II) chloride, copper(I) chloride, copper (0), copper (I) oxide, and copper (II) oxide; ruthenium (Ru) catalysts, such as ruthenium/carbon and ruthenium/alumina; rhodium (Rh) catalysts, such as rhodium/carbon and rhodium/alumina; palladium (Pd) catalysts, such as palladium sponge, palladium black, palladium oxide, palladium/carbon, palladium hydroxide, palladium/barium sulfate, and palladium/barium carbonate; iridium (Ir) catalysts, such as chloro(cyclooctadienyl)iridium dimer; platinum (Pt) catalysts, such as platinum plates, platinum sponge, platinum black, colloidal platinum, platinum oxide, and platinum wires; rhenium (Re) catalysts, such as platinum-supported perrhenic acid; and osmium (Os) catalysts, such as osmium/carbon. The hydrogenation catalyst is preferably a nickel (Ni) catalyst, and more preferably Raney-Ni.

Meanwhile, use of a noble metal catalyst (especially, a rhodium (Rh) catalyst) as a catalyst can reduce the pressure during the reaction and the reaction temperature.

(Reaction Condition)

Specific examples of the production method of the present embodiment include a method in which 5-(halogenated methyl)furfural, an amine compound, a hydrogenation catalyst, and hydrogen are mixed and reacted.

Any order of mixing the 5-(halogenated methyl)furfural, the amine compound, the hydrogenation catalyst, and hydrogen can be employed. From the perspective of operating efficiency, in the production method of the present embodiment, it is preferable to mix beforehand the 5-(halogenated methyl)furfural with the hydrogenation catalyst, then add the amine compound, and then add hydrogen.

In the production method of the present embodiment, addition of the hydrogenation catalyst may be optionally performed in an inert gas atmosphere, such as nitrogen or argon, to prevent ignition, depending on the hydrogenation catalyst used; or the hydrogenation catalyst may be suspended in water and added as a suspension.

In the production method of the present embodiment, the reaction is preferably performed at a hydrogen pressure of more than 0 MPaG and 25 MPaG or less. The hydrogen pressure is more preferably 0.5 MPaG or more, and even more preferably 1.0 MPaG or more. Furthermore, the hydrogen pressure is more preferably 15 MPaG or less, even more preferably 10 MPaG or less, yet even more preferably less than 9 MPaG, and yet even more preferably 8 MPaG or less. The pressure of 15 MPaG or less, less than 9 MPaG, or especially 8 MPaG or less can render the hydrogenation of a ring of the 5-(halogenated methyl)furfural moderate, and thus the bis(aminomethyl)furan can be obtained more easily.

Furthermore, in the case where a noble metal catalyst (especially, a rhodium (Rh) catalyst) is used as a catalyst in the production method of the present embodiment, the reaction can be effectively proceeded even when the reaction is performed at a hydrogen pressure of 3 MPaG or less, or 1.0 MPaG or less.

The ratio of the amine compound to the 5-(halogenated methyl)furfural, in terms of the mole ratio (5-(halogenated methyl)furfural/amine compound), is preferably in a range from 1 to 1000, more preferably in a range from 1 to 500, further preferably in a range of 1 to 100, even more preferably in a range of 1 to 50, and further yet even further more preferably in a range from 1 to 20. Such a range allows the amination to be more effectively proceeded.

The amount of the catalyst relative to the amount of the 5-(halogenated methyl)furfural may be suitably adjusted depending on the type of the substrate to be reacted or the like, and typically is from 1 to 200 mass % relative to the mass of the 5-(halogenated methyl)furfural. The amount of the catalyst is preferably from 1 to 150 mass %, and more preferably from 1 to 100 mass %, relative to the mass of the 5-(halogenated methyl)furfural.

The reaction temperature may be suitably adjusted depending on the type of the substrate to be reacted or the like, and is typically in a range from 40 to 200° C., preferably in a range of 50 to 120° C., and more preferably in a range from 50 to 110° C.

Furthermore, in the case where a noble metal catalyst (especially, a rhodium (Rh) catalyst) is used as the catalyst in the production method of the present embodiment, the reaction can be effectively proceeded even when the reaction temperature is, for example, 10° C. or higher but lower than 40° C., or from 15 to 35° C.

The reaction time may be suitably adjusted by monitoring the progress of the reaction using GC-MS or the like, and is typically from 1 minute to 24 hours, preferably from 0.5 to 3 hours, and more preferably from 0.5 to 2 hours.

The reaction of the present embodiment may be performed in the presence of a solvent. The solvent is not particularly limited and is appropriately selected depending on the reaction temperature, the reaction product, and the like. Examples of the solvent include water; aromatic hydrocarbon-based solvents, such as benzene and toluene; amide-based solvents, such as acetonitrile, N,N-dimethylacetamide and N,N-dimethylformamide; ether-based solvents, such as tetrahydrofuran (hereinafter, also referred to as "THF") and diethyl ether; alcohol-based solvents, such as methanol, ethanol, and isopropanol; and halogen-based solvents, such as dichloromethane, dichloroethane, and chloroform. Among these, an ether-based solvent is preferred. Use of the ether-based solvent renders the solubility of the hydrogen gas in the solvent even better.

One type of these solvents may be used alone, or a combination of two or more types of these solvents may be used.

The use of a solvent or no solvent and the used amount thereof may be appropriately selected considering other reaction conditions and are not particularly limited. From the perspectives of productivity and energy efficiency, the used amount, in terms of mass, is preferably from 0.5 to 100 times, more preferably from 1.0 to 50 times, and even more preferably from 1.0 to 20 times, of the mass of the 5-(halogenated methyl) furfural.

The separation of the reaction mixture from the catalyst after the reaction can be performed by a typical method, such as precipitation, centrifugation, or filtration. Depending on the catalyst used, appropriately, the separation of the catalyst is preferably performed in an inert gas atmosphere, such as nitrogen or argon, to prevent ignition. In the present invention, the yield can be 50% or more, or 62% or more, when the mass in the case where the 5-(halogenated methyl) furfural used in the reaction is quantitatively converted to BAF is assigned a value of 100.

Furthermore, in the case where a solvent is used in the reaction, the obtained reaction solution may be optionally concentrated, and then the residue may be used as is as a raw material or an intermediate product, or the reaction mixture may be appropriately post-treated and purified. Specific examples of the method for the post-treatment include well-known purification methods, such as extraction, distillation, and chromatography. A combination of two or more types of these purification methods may be performed.

EXAMPLES

The present invention will be described in further detail hereinafter using Examples, but the present invention is not limited to the following examples.

Example 1

In a pressure-resistant autoclave, 0.5 g of 5-(chloromethyl)furfural, 3 mL of THF, and 0.3 g of Raney-Ni as a catalyst were charged, then 3 g of liquid ammonia was charged therein, and the hydrogen pressure was raised to 4 MPaG. Note that, Raney-Ni suspended in 3 g of water was used.

Thereafter, the reaction was performed while the temperature was maintained at 90° C. for 1 hour, and the pressure-resistant autoclave was cooled with ice water to terminate the reaction.

Under an argon gas stream, the catalyst was removed by filtering the catalyst and the reaction solution, and GC-MS measurement of the filtrate was performed. Note that the GC-MS measurement was performed using a GC-MS spectrometer Agilent 7890BGC/5977 MSD (available from Agilent Technologies, Inc.).

Calculation Method of Product Yield, and Yield

A calibration curve showing the relationship between the detection intensity (area value) of GC-FID and the BAF concentration was created for comparison with the BAF area value of the reaction solution.

Specifically, from the GC-FID detection intensity (area value) of the reaction solution obtained by the GC-FID measurement, the BAF concentration was calculated by using the calibration curve to determine the BAF mass based on the reaction solution mass. When the yield was calculated by assigning a value of 100 to the mass in the case where the 5-(chloromethyl)furfural used in the reaction was quantitatively converted to BAF, the yield was 62%.

Identification Method of Product (Measurement Result of GC-MS)

In the GC-MS measurement, the retention time obtained by measuring the filtrate of Example 1 was identical with the retention time of the BAF standard sample. In the MS analysis, a molecular ion peak for the molecular weight (126), which was the same as BAF, was observed. Furthermore, the fragment ion peak corresponded to the molecular weight (96) of a compound formed as a result of removal of methyl amine at one side from BAF. Based on these results, it was confirmed that BAF was obtained in Example 1.

Example 2

The same procedure as in Example 1 was performed except for changing the catalyst (Raney-Ni) to a Rh/C catalyst (the content of Rh metal was 5 mass % relative to the mass of the carbon carrier), the hydrogen pressure to 0.3 MPaG, and the reaction temperature to 30° C. It was confirmed that BAF was synthesized.

The production method of the present invention can provide 2,5-bis(aminomethyl)furan which is useful as a monomer, which is a raw material for resins, an epoxy resin curing agent, intermediate material for compounds, or the like, and is industrially applicable for production of resins, pharmaceuticals, perfumes, and the like.

The invention claimed is:

1. A production method for 2,5-bis(aminomethyl)furan, comprising:
    reacting 5-(halogenated methyl)furfural with hydrogen and an amine compound using a hydrogenation catalyst in a one-pot reductive amination reaction to obtain 2,5-bis(aminomethyl)furan; and
    separating 2,5-bis(aminomethyl)furan from the catalyst.

2. The production method according to claim 1, wherein the 5-(halogenated methyl)furfural is 5-(chloromethyl)furfural.

3. The production method according to claim 1, wherein the 5-(halogenated methyl)furfural is derived from at least one type selected from the group consisting of woody biomass, cellulose, and C6 saccharides that are saccharides having 6 carbon atoms.

4. The production method according to claim 1, wherein the amine compound is ammonia or an amide represented by $RCONH_2$, where R represents a hydrogen atom or $-C_nH_{2n+1}$ where n is an integer of 1 or more.

5. The production method according to claim 1, wherein the hydrogenation catalyst is a catalyst containing at least one type selected from the group consisting of Fe, Co, Ni, Cu, Ru, Rh, Pd, Ir, Pt, Re, and Os.

6. The production method according to claim 1, wherein the reaction is performed at a hydrogen pressure of more than 0 MPaG and 25 MPaG or less.

7. The production method according to claim 1, wherein the reaction is performed at a hydrogen pressure of more than 0 MPaG and less than 9 MPaG.

8. The production method according to claim 2, wherein the 5-(halogenated methyl)furfural is derived from at least one type selected from the group consisting of woody biomass, cellulose, and C6 saccharides that are saccharides having 6 carbon atoms.

9. The production method according to claim 2, wherein the amine compound is ammonia or an amide represented by $RCONH_2$, where R represents a hydrogen atom or $-C_nH_{2n+1}$ where n is an integer of 1 or more.

10. The production method according to claim 2, wherein the hydrogenation catalyst is a catalyst containing at least one type selected from the group consisting of Fe, Co, Ni, Cu, Ru, Rh, Pd, Ir, Pt, Re, and Os.

11. The production method according to claim 2, wherein the reaction is performed at a hydrogen pressure of more than 0 MPaG and 25 MPaG or less.

12. The production method according to claim 2, wherein the reaction is performed at a hydrogen pressure of more than 0 MPaG and less than 9 MPaG.

13. The production method according to claim 3, wherein the amine compound is ammonia or an amide represented by $RCONH_2$, where R represents a hydrogen atom or $-C_nH_{2n+1}$ where n is an integer of 1 or more.

14. The production method according to claim 3, wherein the hydrogenation catalyst is a catalyst containing at least one type selected from the group consisting of Fe, Co, Ni, Cu, Ru, Rh, Pd, Ir, Pt, Re, and Os.

15. The production method according to claim 3, wherein the reaction is performed at a hydrogen pressure of more than 0 MPaG and 25 MPaG or less.

16. The production method according to claim 3, wherein the reaction is performed at a hydrogen pressure of more than 0 MPaG and less than 9 MPaG.

17. The production method according to claim 4, wherein the hydrogenation catalyst is a catalyst containing at least one type selected from the group consisting of Fe, Co, Ni, Cu, Ru, Rh, Pd, Ir, Pt, Re, and Os.

18. The production method according to claim 4, wherein the reaction is performed at a hydrogen pressure of more than 0 MPaG and 25 MPaG or less.

19. The production method according to claim 4, wherein the reaction is performed at a hydrogen pressure of more than 0 MPaG and less than 9 MPaG.

20. The production method according to claim 5, wherein the reaction is performed at a hydrogen pressure of more than 0 MPaG and 25 MPaG or less.

21. The production method according to claim 5, wherein the reaction is performed at a hydrogen pressure of more than 0 MPaG and less than 9 MPaG.

22. The production method according to claim 6, wherein the reaction is performed at a hydrogen pressure of more than 0 MPaG and less than 9 MPaG.

* * * * *